United States Patent
Raffa et al.

(10) Patent No.: US 6,900,189 B2
(45) Date of Patent: May 31, 2005

(54) ANALGESIC AND GLUCOSAMINE COMPOSITIONS

(76) Inventors: Robert Raffa, 4 Pacer La., Norristown, PA (US) 19401-1732; Alan Cowan, 549 Mellisa Dr., Ambler, PA (US) 19002; Ronald Tallarida, 6 Merion Way, Mantua, NJ (US) 08051

( * ) Notice: Subject to any disclaimer, the term of this patent is extended or adjusted under 35 U.S.C. 154(b) by 0 days.

(21) Appl. No.: 09/964,178

(22) Filed: Sep. 25, 2001

(65) Prior Publication Data

US 2002/0058642 A1 May 16, 2002

Related U.S. Application Data

(60) Provisional application No. 60/235,405, filed on Sep. 26, 2000.

(51) Int. Cl.[7] .................. A61K 31/192; A61K 31/7008
(52) U.S. Cl. ........................................ 514/62; 514/570
(58) Field of Search ................... 514/570, 62

(56) References Cited

U.S. PATENT DOCUMENTS

| | | | |
|---|---|---|---|
| 3,008,874 A | 11/1961 | Feeney et al. ............... 514/62 |
| 4,501,727 A | 2/1985 | Armitage et al. ............ 424/16 |
| 4,571,400 A | 2/1986 | Arnold ..................... 514/282 |
| 4,647,453 A | 3/1987 | Meisner ..................... 424/54 |
| 4,748,174 A | 5/1988 | Veronesi ................. 514/226.5 |
| 4,772,591 A | 9/1988 | Meisner ..................... 514/62 |
| 4,873,092 A | 10/1989 | Azuma et al. ............... 424/499 |
| 4,880,921 A | 11/1989 | Bodor ....................... 540/110 |
| 4,917,886 A | 4/1990 | Asche et al. ................ 424/81 |
| 5,364,845 A | 11/1994 | Henderson .................. 514/54 |
| 5,380,922 A | 1/1995 | Beach et al. ................ 562/467 |
| 5,587,363 A | 12/1996 | Henderson .................. 514/54 |
| 5,604,206 A | 2/1997 | Paradies .................... 514/23 |
| 5,654,337 A * | 8/1997 | Roentsch et al. ............ 514/570 |
| 5,679,344 A | 10/1997 | Williams et al. ............ 424/94.63 |
| 5,811,410 A * | 9/1998 | Falk et al. .................. 514/54 |
| 5,830,432 A | 11/1998 | Chasalow ................... 424/1.77 |
| 5,840,715 A | 11/1998 | Florio ....................... 514/62 |
| 5,843,919 A | 12/1998 | Burger ...................... 514/62 |
| 5,916,910 A | 6/1999 | Lai .......................... 514/423 |
| 5,972,999 A | 10/1999 | Murad ....................... 514/474 |
| 6,069,172 A | 5/2000 | Bertini et al. ............... 514/570 |
| 6,291,527 B1 * | 9/2001 | Giorgetti .................... 514/570 |
| 6,399,093 B1 * | 6/2002 | Petrus ....................... 424/448 |
| 6,608,041 B2 * | 8/2003 | Hammerly ................... 514/54 |
| 6,841,544 B2 | 1/2005 | Gelber et al. |

FOREIGN PATENT DOCUMENTS

| | | |
|---|---|---|
| EP | 0 935 961 A2 | 8/1999 |
| WO | WO 93/23055 | 11/1993 |
| WO | WO 99/52528 | 10/1999 |
| WO | WO 99/62524 | 12/1999 |

OTHER PUBLICATIONS

Alvin Last Inc., "Born Again Glucosamine Pain Relieving Roll–On with Capsaicin and Chondroitin; Glucosamine Pain Relieving Crème with Capsaicin", Product Alert, vol. 27, No. 19, Oct. 13, 1997, p. 129, XP002171695, Abstract.
International Search Report 2004.

* cited by examiner

*Primary Examiner*—James O. Wilson
*Assistant Examiner*—Leigh C. Maier
(74) *Attorney, Agent, or Firm*—RatnerPrestia

(57) ABSTRACT

This invention relates to a composition comprising a glucosamine material and an analgesic compound such as a nonsteroidal anti-inflammatory drug (NSAID) and/or an opioid analgesic and its use for treatment of pain in pharmaceutical or veterinary applications. When the components of the compositions are administered within certain ratios, the analgesic efficacy of the composition is super-additive (synergistic) relative to the analgesic efficacy of the analgesic compound alone.

7 Claims, 3 Drawing Sheets

Probit plots of ibuprofen alone (Ibu) and ibuprofen in fixed-ratio combination with glucosamine sulfate(Comb).

Fixed Ibuprofen Dosage with Variable Amounts of Glucosamine sulfate.

Probit plots of aspirin (ASA) alone and aspirin in combination with glucosamine sulfate (ASA+Gluc.).

ANALGESIC AND GLUCOSAMINE COMPOSITIONS

This application claims the benefit of provisional application 60/235,405 filed on Sep. 26, 2000.

FIELD OF THE INVENTION

The invention relates to analgesic compositions which comprise a glucosamine material in combination with an analgesic compound. Depending on the choice of analgesic compound and the weight ratio of glucosamine to analgesic compound, the analgesic efficacy of the composition may be either additive or super-additive.

BACKGROUND OF THE INVENTION

Drugs such as aspirin, ibuprofen, acetaminophen, and morphine are used as analgesics. Ibuprofen, aspirin and other analgesic nonsteroidal anti-inflammatory drugs (commonly referred to as NSAIDs) and acetaminophen are only useful in relieving pain of moderate intensity, whereas opioid analgesics such as morphine are useful in relieving more intense pain. However, opioids exhibit side-effects including addictive properties, and ibuprofen, aspirin, other NSAIDs and acetaminophen can cause serious gastrointestinal, renal, and cardiovascular side effects, especially when used in high doses and/or over long periods of time.

NSAIDs, which are non-opioid analgesics, have been combined with other drugs, including opioid analgesic agents, in order to achieve an effective degree of analgesia with a lower dosage of NSAID and/or other analgesic compound. These combination products exhibit a variety of effects on the level of analgesia, which may be sub-additive (inhibitory), additive, or super-additive (synergistic). For example, U.S. Pat. No. 4,571,400 discloses that the combination of dihydrocodeine (an opioid analgesic) and ibuprofen (an NSAID) provides super-additive analgesia when the components are combined within certain ratios. A. Pircio et al., Arch. Int. Pharmacodyn., 235,116 (1978) report that a mixture of butorphanol (an opioid analgesic) with acetaminophen (a non-opioid analgesic) in a 1:125 ratio yielded super-additive analgesia, but that a 1:10 mixture of the same components yielded merely additive analgesic effects. A combination of tolmetin (an NSAID) with acetaminophen (a non-opioid analgesic) has been reported to enable a marked reduction in the amount of tolmetin required to produce analgesia (G. Stacher et al., Int. J. Clin. Pharmacol. Biopharmacy, 17, 250 (1977)). However, it is also known that the daily consumption of non-opioid analgesics, either alone or in combination, in large amounts or over time also poses health risks. Moreover, it is known that the effects on the level of analgesia obtained when combining such analgesics is highly unpredictable, depending on the choice of analgesics combined and the ratios at which they are combined. Specifically, a particular combination may provide a sub-additive level of analgesia.

Glucosamine is an essential intermediate in the biosynthetic pathway of proteoglycans, which are the primary building blocks of connective tissue and cartilage. Glucosamine compounds exhibit weak anti-inflammatory activity, but no analgesic activity. Glucosamine in combination with manganese and chondroitin, which is also a component of proteoglycans, is currently marketed as a nutritional supplement to enhance the repair and synthesis of connective tissue and cartilage (See U.S. Pat. Nos. 5,364, 845; 5,587,363; 5,840,715). Glucosamine combined with ascorbic acid, tyrosine or phenylalanine, and calcium has been shown to accelerate wound healing (See U.S. Pat. Nos. 4,647,453; 4,772,591; and 5,679,344). Glucosamine has also been used to improve the solubility of NSAIDs by combining a glucosamine with an NSAID in a 1:1 molar ratio to form a glucosamine salt or complex with the NSAID, but the analgesic effect (whether sub-additive, additive or synergistic) has not been reported for these complexes (See U.S. Pat. Nos. 4,501,727; 5,604,206; and 6,069,172). In addition, aspirin plus glucosamine has been disclosed in U.S. Pat. No. 3,008,874 to enhance the blood level of aspirin, specifically at glucosamine to aspirin weight ratios of 0.25:1 and 0.77:1. As with the prior art cited above relating to glucosamine: NSAID complexes, there is no disclosure of the analgesic effect of these compositions.

Numerous studies have compared the pain relief achieved in arthritic conditions from the use of glucosamine with the pain relief achieved with various analgesic compounds alone, but there has been no suggestion to use glucosamine and an analgesic compound of this invention together in order to obtain additive or super-additive analgesia. To the contrary, the scientific literature uniformly emphasizes the need to replace NSAIDs with glucosamine, while the marketing of glucosamine products most often emphasizes that the product does not contain analgesic. Further to the contrary, it has been shown that when glucosamine is combined at certain ratios, for example with aspirin, diclofenac or tramadol (a centrally acting non-opioid analgesic), the analgesic efficacy of analgesic is reduced (i.e., the combination is sub-additive) by as much as 80%, as discussed below. Accordingly, one skilled in the art cannot predict whether a combination of glucosamine with an analgesic will produce sub-additive analgesia, additive analgesia, or super-additive analgesia.

Nevertheless, a need exists to both decrease the side effects and enhance the analgesic effects of analgesics such as opioids, non-opioid analgesics, and NSAIDs. The object of the present invention is to combine glucosamine with a therapeutic amount of an analgesic compound to provide an analgesic composition which provides analgesia at least equal to and in many cases substantially greater than that of the analgesic compound alone. In the preferred embodiments of this invention the analgesic compound and the ratio of glucosamine to analgesic compound are selected to avoid significant sub-additive analgesic effects which can occur when two or more analgesics are combined or when an analgesic, such as diclofenac or tramadol, is combined with glucosamine. In the preferred embodiment, the combination of glucosamine with an analgesic compound at an appropriate ratio will synergistically enhance the analgesic effect of the analgesic compound, such as an NSAID, so that less analgesic compound is needed to produce effective analgesia, and potential side-effects are accordingly reduced. In addition the combination of glucosamine with an analgesic is also expected to retain its beneficial effects on restoration and maintenance of cartilage.

SUMMARY OF THE INVENTION

The present invention provides a dosage form which combines a glucosamine material with an analgesic compound, preferably to produce a level of analgesia which is at least as high as that for the analgesic compound alone, that is, either additive or super-additive analgesia. When employed at appropriate ratios, the combination employs a lower amount of analgesic compound than would be necessary to produce the same level of analgesia with the analgesic used alone. By using less analgesic compound, undesirable side effects are reduced in number and degree. Surprisingly, the compositions comprising the glucosamine material and one or more analgesics exhibit super-additive (or synergistic) analgesia effects when the components are combined in certain ratios.

The present invention thus provides a dosage form comprising a glucosamine material and a therapeutic amount of an analgesic compound wherein the analgesic efficacy of the analgesic compound is not significantly reduced by the glucosamine material; that is, the analgesic efficacy of the combination is at least equal to the analgesic efficacy of the analgesic alone, in addition to providing the additional benefit of glucosamine. By properly selecting the analgesic compound and the weight ratio of the glucosamine material to the analgesic compound one skilled in the art may conveniently design dosage forms in which the analgesic efficacy is at least additive. In the preferred embodiments of the present invention the combination produces super-additive analgesia as further described below.

DETAILED DESCRIPTION OF THE INVENTION

Figure 1:
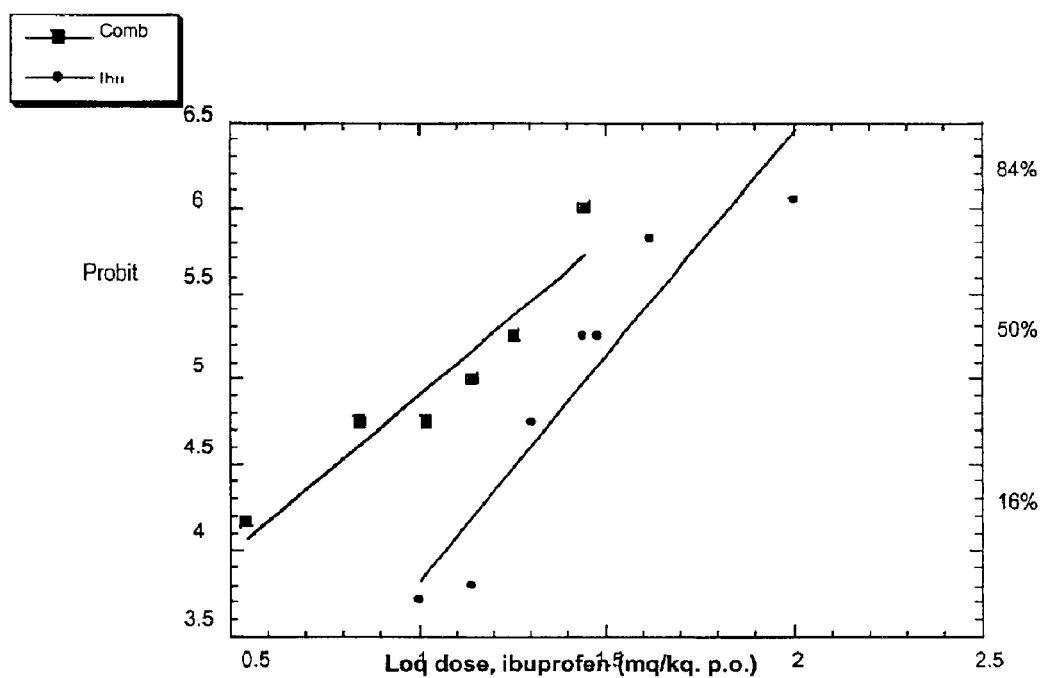
FIG. 1 is a graph showing the analgesic effect of a composition comprising glucosamine sulfate and ibuprofen on acetylcholine induced abdominal constriction in mice, illustrating a marked enhancement of the analgesic efficacy of ibuprofen in the presence of glucosamine.
Figure 2:
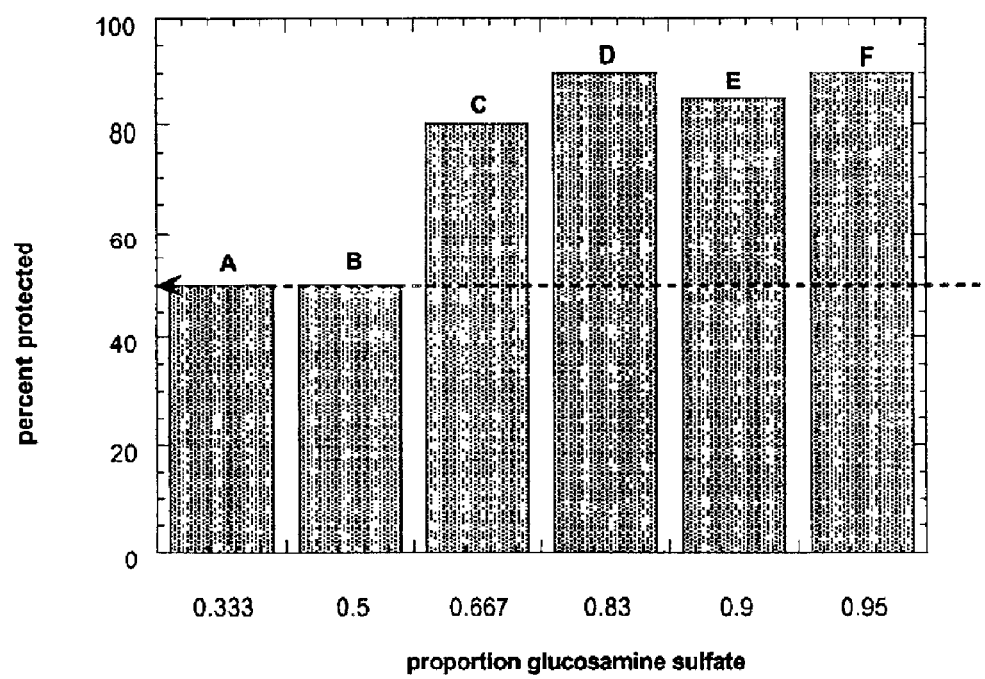
FIG. 2 is a graph showing the analgesic effect of a composition comprising various dosages of glucosamine sulfate and a fixed dosage of ibuprofen on acetylcholine induced abdominal constriction in mice, illustrating a marked enhancement of the analgesic efficacy of ibuprofen in the presence of sufficient dosages of glucosamine.

The present invention is directed to dosage forms comprising a glucosamine material and an effective analgesic amount of an analgesic compound, for example an NSAID. Glucosamine compounds alone have no analgesic activity. However, when combined with some NSAIDs or other analgesic compounds in a particular ratio, the combination exhibits an analgesic efficacy at least equal to the analgesic efficacy of the analgesic compound alone, and in many instances may produce an unexpected synergistic increase in the analgesic efficacy of the analgesic compound or compounds employed in the combination. The combination may be used for the relief of pain, for example, pain associated with influenza and colds, arthritis, headache, toothache, dysmenorrhea, and surgery as well as muscular and joint pain.

Glucosamine is 2-amino-2-deoxy-D-glucose. The structure of glucosamine, as well as methods of isolation and synthesis of glucosamine, are well-known in the art. Glucosamine is an essential intermediate in the biosynthetic pathway of chondroitin and proteoglycans, which are the primary building blocks of cartilage and connective tissue. Glucosamine compounds exhibit weak anti-inflammatory activity, but no analgesic activity. No undesirable side-effects of glucosamine therapies have been established. In compositions of the present invention, the glucosamine material may be one or more of the following: the α- or β-form of glucosamine or mixtures thereof, N-acetylglucosamine, or various pharmaceutically acceptable salts of any of them, in particular glucosamine sulfate or glucosamine HCl. It is understood that the present invention does not include salts or complexes of glucosamine which have a counter ion which has analgesic activity of its own.

NSAIDs useful in the present invention are non-opioid analgesics which are characterized as nonsteroidal drugs which act as anti-inflammatory, analgesic and anti-pyretic agents. This class of drugs is well known in the art. These drugs share certain therapeutic actions and side effects. Within this broad class of drugs those which may be suitable for use in the present invention include pyrazolone derivatives such as phenylbutazone, oxyphenbutazone, antipyrine, aminopyrine, dipyrone and apazone; indomethacin; sulindac; fenamates such as mefenamic, meclofenamic, flufenamic, tolfenamic and etofenamice acids; aryl acetic acid and propionic acid compounds such as 2-(p-isobutylphenyl)propionic acid (ibuprofen); alphamethyl-4-(2-thienylcarbonyl) benzene acetic acid (suprofen); 4,5-diphenyl-2-oxazole propionic acid (oxprozin); rac-6-chloro-alphamethyl-carbazole-2-acetic acid (carprofen); 2-(3-phenyloxyphenyl)-propionic acid, particularly the calcium salt dihydrate thereof (fenoprofen and fenoprofen calcium); 2-(6-methoxy-2-naphthyl) propionic acid (naproxen); 4-(1, 3-dihydro-1-oxo-2H-isoindol-2yl)-alpha-methylbenzene acetic acid (indoprofen); 2-(3-benzoylphenyl)propionic acid (ketoprofen); and 2-(2-fluoro-4-biphenylyl)propionic acid (flurbiprofen) and 1-5-(4-methylbenzoyl)-1H-pyrrole-2-acetic acid (tolmetin). Also included within NSAIDs are compounds within the class including sodium 5-(4-chlorobenzoyl)-1,4-dimethyl-1H-pyrrole-2-acetate dihydrate (zomepirac sodium); 4-hydroxy-2-methyl-N-(2-pyridyl-2H-1,2-benzothiazine-3-carboxamide- 1,1-dioxide (piroxicam); 2', 4'-difluoro-4-hydroxy-3-biphenylcarboxylic acid (diflunisal) or 1-isopropyl-7-methyl-4-phenyl-2(1H)-quinozolinone (proquazone), and Cox-2 inhibitors such as rofecoxib and celecoxib. All of the foregoing are commercially available materials. A particularly preferred class of NSAIDs for use in the composition of the present invention is the propionic acid derivatives. Within this class of compounds, ibuprofen and ketoprofen are of particular interest.

Other analgesic compounds suitable for use in the present invention, either alone or in combination with each other or with other analgesics are opioid analgesics. Such opioid analgesics are well known to those skilled and in the art and include, for example codeine, morphine, dihydrocodeine, butorphanol, etc. Thus, the compositions of this invention include those wherein the analgesic compound is an opioid analgesic, a non-opioid analgesic, or an NSAID, including physiologically active and pharmaceutically acceptable salts and isomers thereof.

In the compositions of the present invention, it is contemplated that one or more analgesic compounds and/or one or more types of analgesic compounds may be employed. Thus when an NSAID is employed, the NSAID component of the composition may either be a single NSAID or a combination of one or more NSAIDs. The NSAID or other analgesic and the glucosamine material are generally present in a weight ratio of glucosamine to analgesic of at least 1:2, for example 1:1 or above, but may be varied widely within certain limits discussed below. However, it is critical to this invention that the ratios selected for a particular analgesic or combination of analgesics is such that, at that ratio, analgesic efficacy of the composition is at least equal to that of the analgesic compound or compounds alone; that is, the analgesic efficacy is not significantly depressed below the level of analgesic efficacy of the analgesic compound or combination of analgesic compounds alone, in absence of the glucosamine. The determination of a desirable ratio is well within the skill of the art without undue experimentation, and may be ascertained by the tests described in detail below. In general, the desired level of analgesic efficacy may be obtained when the weight ratio of glucosamine to analgesic compound is selected from within the range of about 1:10 to about 100:1, advantageously in the range of 1:1 to about 20:1 if based on the composition employed in the examples or about 1:2 to 10:1 if based on glucosamine per se.

Certain ratios of glucosamine to analgesic compound result in a composition which exhibits synergistic analgesic effects. For example, in a composition comprising giucosamine sulfate and an NSAID such as Ibuprofen, a glucosamine sulfate:ibuprofen ratio up to 1:1 produces essentially additive analgesia, whereas a ratio that is between about 1:1 and 2:1 or higher, up to 20:1 has been shown to produce super-additive analgesia, as shown In the examples and figures. Stated otherwise, based on glucosamine per se, a glucosamine:ibuprofen ratio of 1:2 produces essentially additive analgesia, whereas at a ratio which is greater than 1:2, that is between 1:2 and 1:1, such compositions produce super-additive analgesia and continue to do so at even higher ratios, for example up to about 10:1. Suitably the glucosamine sulfate: ibuprofen weight ratio is at least 1.2:1, for example 2:1; at least 4:1, for example 5:1, at least 8:1, for example 9:1; or for example at least 15:1, such as 19:1, based one the glucosamine sulfate composition used In exemplifying this invention, as further described below.

The glucosamine/analgesic formulations of this invention may also comprise therapeutically effective amounts of one or more other pharmaceutical actives including, but not limited to, antiarthritics such as chondroitin, decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof), antihistamines (such as chlorpheniramine, brompheniramine, dexchlorpheniramine, dexbromphreniramine, triprolidine, doxylamine, tripelennamine, cyproheptadine, hydroxyzine, pyrilamine, azatadine, promethazine and pharmaceutically acceptable salts thereof), non-sedating antihistamines (such as acrivastine, astemizole, cetirizine, ketotifen, loratidine, temelastine, terfenadine, including the metabolites disclosed in U.S. Pat. Nos. 4,254,129 and 4,284,957, hereby incorporated by reference, and pharmaceutically acceptable salts thereof), muscle relaxants (such as glycerylmonether SMRS, methocarbamol, mephenesin, mephenesin carbamate, mephenesin acid succinate, cyclobenzaprine, chlorphenesin carbamate, chlorzoxazone or pharmaceutically acceptable salts thereof) and suspected adjuvants (such as diphenhyhdramine, caffeine, xanthine derivatives (including those disclosed in U.S. Pat. No. 4,558,051, hereby incorporated by reference) and pharmaceutically acceptable salts thereof), and combinations of any of the aforesaid pharmaceuticals. The aforesaid pharmaceuticals may be included in formulations for the treatment of such ailments as allergies, sleep disorders, cough, colds, cold and/or flu symptoms, and arthritic and joint pain in mammals including humans.

Pharmaceutical compositions comprising the glucosamine material and an analgesic compound such as an NSAID and, when desired, other pharmaceutical actives in an admixture with a pharmaceutical carrier can be prepared according to conventional pharmaceutical compounding techniques. The carrier may take a wide variety of forms depending on the form of preparation desired for administration, e.g., oral, rectal, parenteral, topical. The composition may also be administered by means of an aerosol or a cachet.

In preparing the compositions in an oral dosage form, any of the usual pharmaceutical media may be employed. For example, in the case of oral liquid preparations (such as suspensions, elixirs and solutions), water, glycols, oils, alcohols, flavoring agents, preservatives, coloring agents and the like may be used. In the case of oral solid preparations (such as, for example, powders, capsules and tablets and cachets), carriers such as starches, sugars, diluents, granulating agents, lubricants, binders, disintegrating agents and the like, may be used.

Because of their ease in administration, tablets and capsules represent the most advantageous oral dosage unit form, in which case solid pharmaceutical carriers are obviously employed. If desired, tablets may be sugar-coated or enteric-coated by standard techniques. For parenteral formulations, the carrier will usually comprise sterile water, although other ingredients, for example, to aid solubility or for preservative purposes, may be included. Injectable suspensions may also be prepared, in which case appropriate liquid carriers, suspending agents and the like may be employed.

The pharmaceutical compositions will generally be administered in the form of a dosage unit, e.g., one or more tablet(s), capsule(s), sachet(s), ampoule(s), teaspoon(s), etc., containing from 0.1 to about 800 mg/kg, and preferably from about 0.3 mg to 200 mg/kg of the NSAID or other analgesic compound. The analgesic compound and the glucosamine material in a dosage unit may be incorporated into the same or different components thereof. For example, if the dosage unit is in the form of tablet(s), then the analgesic compound and the glucosamine may be incorporated together into the same tablet(s) or they may be each incorporated separately into different tablets. The dosage unit is calculated based on the amount of active ingredient which may be given to a 70 kg human subject in a single dose. The pharmaceutical compositions may be given at a daily dosage of from about 10 to 6000 mg/kg/day. However, it will be appreciated that the precise dose of the active ingredients will vary depending upon the particular NSAID or other analgesic and glucosamine material being used and on the condition being treated.

When one or more other pharmaceutical components are added to the glucosamine/analgesic composition, those components may be added in therapeutically effective amounts known in the art and may be given at dosages conventional for such components. For example, decongestants and bronchodilators may be given in a single dosage of from about 12.5 to 75 mg/kg and at a daily dosage of from about 60 to 150 mg/kg/day. Antitussives may be given in a single dosage of from about 2.5 to 30 mg/kg and at a daily dosage of from about 20 to 120 mg/kg/day. Antihistamines may be given in a single dosage of from about 1 to 50 mg/kg and at a daily dosage of from about 4 to 600 mg/kg/day. Non-sedating antihistamines may be given in a single dosage of from about 8 to 30 mg/kg and at a daily dosage of from about 30 to 120 mg/kg/day. Muscle relaxants may be given at a single dosage of from about 10 to 1500 mg/kg and at a daily dosage of from about 60 to 8000 mg/kg/day. Adjuvants may be given in a single dosage of from about 1 to 25 mg/kg and at a daily dosage of from about 1 to 100 mg/kg/day.

The following examples describe the invention in greater detail and are intended to illustrate, but not limit, the invention. In the following examples, weights, doses and ratios of glucosamine are reported based on a glucosamine material comprising glucosamine sulfate, the glucosamine (i.e. 2-amino-2-deoxy-D-glucose) content of which is 58% by weight of the glucosamine material. Thus, for example a "glucosamine sulfate to ibuprofen ratio" of 1:1 corresponds to a "glucosamine to ibuprofen ratio" of 0.58:1. In the examples which follow, this glucosamine material is expressed as glucosamine sulfate.

EXAMPLE 1

Preparation of the Combined Doses of Glucosamine and Ibuprofen

Solutions of glucosamine/ibuprofen combinations with different ratios were prepared and concentrations of each component expressed as mg per 10 mL of distilled water. For example, 250 mg of glucosamine sulfate and 27.8 mg of ibuprofen were added to 10 mL of water with 2 drops of TWEEN®-80, a pharmacological dispersant, to yield a glucosamine sulfate to ibuprofen weight ratio of 9:1 (250mg: 27.8mg), which corresponds to a glucosamine to ibuprofen weight ratio of about 5.2:1.

EXAMPLE 2

Preparation of the Combined Doses of Glucosamine and Diclofenac

Solutions of glucosamine and diclofenac with different ratios were prepared and concentrations of each component expressed as mg per 10 mL of distilled water. For example, 250 mg of glucosamine sulfate and 2.288 mg of diclofenac were added to 10 mL of water with 2 drops of TWEEN®-80, a pharmacological dispersant, to yield a glucosamine sulfate to diclofenac weight ratio of 109:1 (250 mg:2.288 mg), which corresponds to a glucosamine to diclofenac weight ratio of about 63:1.

EXAMPLE 3

Preparation of the Combined Doses of Glucosamine and Tramadol

Solutions of glucosamine/tramadol combinations with different ratios were prepared and concentrations of each component expressed as mg per 10 mL of distilled water. For example, 250 mg of glucosamine sulfate and 10 mg of tramadol HCL were added to 10 mL of water with 2 drops of TWEEN®-80, a pharmacological dispersant, to yield a glucosamine sulfate to tramadol weight ratio of 25:1 (250 mg: 10 mg), which corresponds to a glucosamine to tramadol weight ratio of about 15:1.

EXAMPLE 4

Preparation of the Combined Doses of Glucosamine and Acetaminophen

Solutions of glucosamine/acetaminophen combinations with different ratios were prepared and concentrations of each component expressed as mg per 10 mL of distilled water. For example, 112.5 mg of glucosamine sulfate and 112.5 mg of acetaminophen were added to 10 mL of water with 2 drops of TWEEN®-80, a pharmacological dispersant, to yield a glucosamine sulfate to acetaminophen weight ratio 1:1 (112.5 mg:112.5 mg), which corresponds to a glucosamine to acetaminophen weight ratio of about 0.58:1.

EXAMPLE 5

Testing for Analgesic Activity

Mature, male Swiss-Webster mice (weighing 25–30 g) were utilized in determining the analgesic effects of the compositions. The mice were all dosed orally with glucosamine sulfate, which was completely dissolved in distilled water, and a selected analgesic (ibuprofen, diclofenac, tramadol HCl, or acetaminophen), which was completely dissolved in distilled water or in distilled water containing 2% by volume of TWEEN®-80 containing 100% polysorbate 80. Mice were dosed at 10 mL/kg.

The procedure used in detecting and comparing the analgesic activity of different classes of analgesic drugs was the prevention of acetylcholine induced abdominal constriction in mice. Effective compounds will protect the mouse from the acetylcholine induced abdominal constriction. This animal model assay correlates well with human analgesic efficacy. (H. Collier et al., Br. J. Pharmacol., 32, 295 (1968)).

Mice were treated with various doses of glucosamine sulfate alone, analgesic alone, combined doses of glucosamine sulfate and analgesic, or vehicle such as distilled water containing 2% by volume of TWEEN®-80. Intraperitoneal injection of a challenge dose of acetylcholine bromide was administered 30 minutes after treatment. The acetylcholine was completely dissolved in distilled water at a concentration of 5.5 mg/kg and injected at the rate of 0.20 mL/20 g. For scoring purposes an "abdominal constriction" was defined as a contraction of the abdominal musculature accompanied by arching of the back and extension of the limbs. The mice were observed for 10 minutes for the presence or absence of an abdominal constriction response beginning immediately after the acetylcholine injection. Each mouse was tested only once.

The analysis of possible super-additivity (synergism) for each composition was determined as disclosed in publications by Finney (1971), Tallarida et al (1989) and Tallarida (2000). This procedure, based on weighted regression analysis (probit analysis), involves the determination of the amount of analgesic in a mixture that is required to produce a specified level of effect, such as 50% ($ED50_{mix}$), and the corresponding amount of analgesic that is required when only analgesic is used in the test ($ED50_{add}$). Glucosamine sulfate alone produced no response in doses up to 500 mg/kg (twice the highest glucosamine dosage employed in any combination). Because glucosamine sulfate alone has no activity in this test, the analgesic-only dose ($ED50_{add}$) and the mixture dose ($ED50_{mix}$) of analgesic would be expected to be the same. Doses of the combinations were coded to permit complete randomization of the tests.

EXAMPLE 6

Testing of Ibuprofen & Glucosamine

The effects of glucosamine sulfate plus ibuprofen, a propionic acid NSAID, on acetylcholine-induced abdominal constriction in mice are shown in the dose-response curves of FIG. 1. Since glucosamine sulfate lacks activity in this assay, the graphs for ibuprofen alone and for ibuprofen plus glucosamine sulfate would be predicted to be coincident. However, the graph for the combination is shifted to the left, indicating increased protection (super-additive analgesia) as a feature of the ibuprofen-glucosamine sulfate combination. The degree of super-additivity (synergism) is indicated by the potency measured by the dose-response test. Potency is conventionally expressed as ED50 values, i.e., doses that show an effect on 50% (probit 5) of the animals tested. For ibuprofen alone ED50=26.12±3.41 mg/kg (Table 1A, below. However, for ibuprofen combined with glucosamine sulfate, ED50=10.97±2.08 mg/kg (Table 1B, below). These results demonstrate that, contrary to expectations, the effective dose of ibuprofen was reduced by more than half (58%) when administered in combination with a 9:1 ratio of glucosamine sulfate. The difference in ED50 values tested by Student t-distribution was statistically significant, p<0.05; and the difference between the regression lines in FIG. 1 tested by F-distribution was highly significant, p<0.01.

TABLE 1A

Ibuprofen (alone), mg/kg

| Ibuprofen | No. protected/no. tested |
|---|---|
| 10 | 1/10 |
| 13.91 | 1/10 |
| 20.0 | 4/10 |
| 27.8 | 6/10 |
| 30.0 | 6/10 |
| 41.74 | 8/10 |
| 100 | 9/10 |
| ED50 | 26.12 |

TABLE 1B

Ibuprofen, mg/kg, + Glucosamine sulfate, mg/kg

| Ibuprofen | Glucosamine | No. protected/no. tested |
|---|---|---|
| 3.48 | 31.2 | 2/10 |
| 6.96 | 62.5 | 4/10 |
| 10.4 | 93.7 | 4/10 |
| 13.9 | 125 | 5/10 |
| 18.0 | 154 | 6/10 |
| 27.8 | 250 | 17/20 |
| ED50 @ 9:1 ratio | | 10.97 |

In the manner described above, several groups of mice were administered a quantity of ibuprofen at levels approximately equal to its ED50 (26.12 mg/kg) in combination with different amounts of glucosamine. The results of these tests are set forth in Table 1C.

TABLE 1C

| Group | Ibuprofen (mg/kg) | Glucosamine sulfate (mg/kg) | No. protected/no. tested | GLU/IBU Wt. Ratio |
|---|---|---|---|---|
| A | 26.12 | 13.06 | 5/10 | 0.5:1 |
| B | 26.12 | 26.12 | 5/10 | 1:1 |
| C | 26.12 | 52.24 | 8/10 | 2:1 |
| D | 26.12 | 130.6 | 9/10 | 5:1 |
| E | 27.83 | 250 | 17/20 | 9:1 |
| F | 26.12 | 500 | 9/10 | 19:1 |

Groups A and B, in which the ratio of giucosamine sulfate to ibuprofen was 1:1 or less than 1:1, illustrates that at these ratios an ibuprofen/glucosamine combination produces additive analgesia. However, when the ratio of glucosamine sulfate to ibuprofen is increased above 1:1, as in groups C–F, super-additive (synergistic) analgesia results. These data also indicate for ibuprofen that the threshold for synergistic analgesia occurs when the glucosamine sulfate to analgesic weight ratio lies between 1:1 and 2:1 and that super-additivity continues at ratios above that threshold ratio to a ratio at least as high as 20:1.

EXAMPLE 6A

In the manner of Example 6, the S(+) isomer of ibuprofen was tested alone and in combination with glucosamine sulfate. The results are reported in Table 2.

TABLE 2

| Group | S(+) Ibuprofen (mg/kg) | Glucosamine sulfate (mg/kg) | No. protected/ no. tested | GLU/IBU Wt. Ratio |
|---|---|---|---|---|
| A | 15 | — | 2/10 | |
| B | 30 | — | 4/10 | |
| C | 60 | | 6/10 | |
| D | 120 | | 7/10 | |
| E | 47.4 | 474 | 7/10 | 10:1 |
| F | 47.4 | 237 | 6/9 | 5:1 |
| G | 47.4 | 118.5 | 8/10 | 2.5:1 |

The results demonstrate super-additive analgesia with glucosamine/S(+) ibuprofen.

EXAMPLE 7

Testing of Ketoprofen & Glucosamine

Combinations of ketoprofen and glucosamine were tested in the mouse abdominal constriction test described above. The test results are shown in Table 3 for ketoprofen alone and ketoprofen in combination with a fixed weight ratio of glucosamine sulfate to ketoprofen of 2.63:1

TABLE 3

| Ketoprofen (mg/kg) | Glucosamine sulfate (mg/kg) | No. protected/ no. treated |
|---|---|---|
| 30 | — | 2/10 |
| 60 | — | 4/10 |
| 120 | — | 6/10 |
| 240 | — | 7/10 |
| 23.75 | 62.5 | 5/10 |
| 35.63 | 93.25 | 6/10 |
| 47.5 | 125 | 7/10 |

In the foregoing test ketoprofen alone had an ED50 value of 94.8 mg/kg when used alone, whereas in a 2.63:1 ratio with glucosamine sulfate it had an ED50 value of 24.2 mg/kg. Since glucosamine sulfate alone is inactive in this test, the results clearly indicate that ketoprofen and glucosamine combined provide a super-additive (synergistic) combination.

Table 4 shows the results of assays of combinations of aspirin and glucosamine sulfate, acetaminophen and glucosamine sulfate, diclofenac and glucosamine sulfate, tramadol HCl and glucosamine sulfate, and indomethacin and glucosamine sulfate. Treatment doses were selected based on the ED50 for each analgesic compound given alone.

Figure 3:
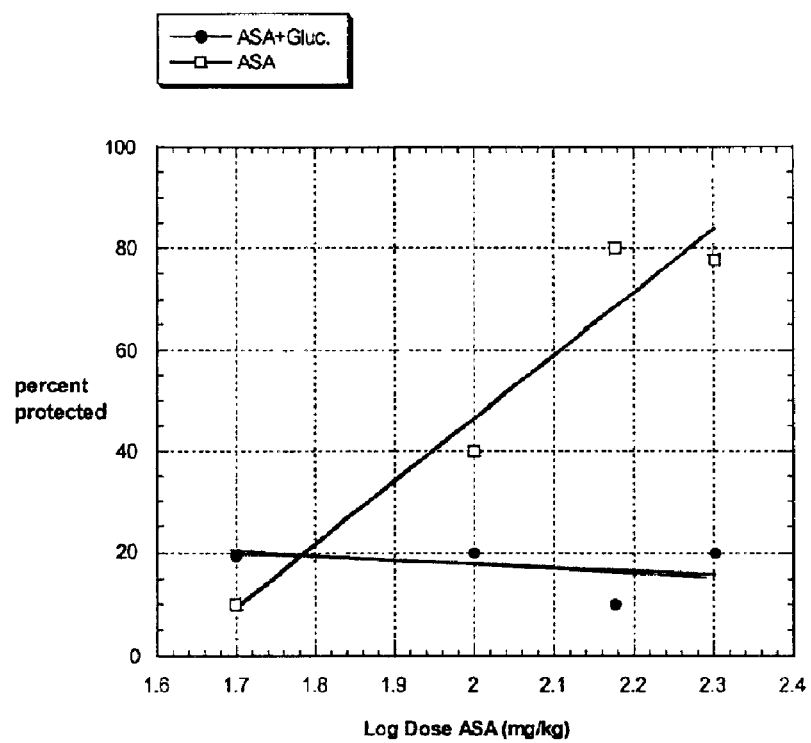
FIG. 3 is a graph showing, for comparative purposes, the analgesic effect of a composition comprising aspirin and glucosamine sulphate on acetylcholine induced abdominal constriction in mice, illustrating a marked depression of the analgesic efficacy of aspirin in the presence of glucosamine.

Aspirin alone showed an ED50 of 109.2 mg/kg. The combination of ASA with glucosamine sulfate in a fixed glucosamine sulfate to ASA ratio of 2.5:1 reduced the analgesic efficacy of aspirin to approximately 20% of the value of aspirin alone. Thus the efficacy was severely depressed by the presence of glucosamine sulfate, as shown in FIG. 3.

For acetaminophen alone compared acetaminophen in combination with glucosamine sulfate, the data demonstrate that acetaminophen does not exhibit a super-additive analgesic effect in combination with glucosamine sulfate, in general appears to exhibit sub-additive analgesia, but may exhibit additive analgesia at selected dosages and ratios.

Similarly, when either diclofenac or tramadol HCl was combined with glucosamine sulfate, the analgesic efficacy of either analgesic compound was substantially reduced at the ratios tested. For example, when 1.144 mg/kg of diclofenac (the ED50 value for diclofenac alone) was used in combination with 125 mg/kg of glucosamine sulfate, only 5 out of 20 animals were protected, one-half of the protection achieved when the same dosage of diclofenac is used alone. The limited data further suggest an ED50=1.96 mg/kg for the combination, roughly a 70% increase in the effective analgesic dosage of diclofenac that is required when administered in combination with glucosamine sulfate at the concentrations tested, a clear case of sub-additivity. As another example, when tramadol HCl was used in combination with glucosamine sulfate, the analgesic efficacy of tramadol HCl was reduced such that the 50% effect level (5/10 animals protected) could not be achieved even with the combination containing 10 mg/kg of tramadol HCl, a tramadol HCl dosage greater than the ED50=8.05 mg/kg value of tramadol HCl when used alone, i.e., another clear case of sub-additivity. Thus, combinations of glucosamine with aspirin, acetaminophen, diclofenac or tramidol at those ratios are sub-additive and thus are, by definition, excluded from the scope of the invention and from the claims set forth below, but serve to demonstrate the point that it is not obvious that combining a glucosamine material with an analgeisic results in analgesic efficacy that is at least additive.

In the claims which follow the ratios are expressed as weight of glucosamine sematerial, calculated and reported in the following examples based on an equivalent amount glucosamine sulfate, to weight of analgesic unless explicitly stated otherwise.

TABLE 4

Aspirin (ASA), mg/kg + Glucosamine sulfate, mg/kg[a]

| ASA | Glucosamine | No. protected/no. tested |
|---|---|---|
| 50 | — | 1/10 |
| 100 | — | 4/10 |
| 150 | — | 8/10 |
| 200 | — | 7/10 |
| 50 | 125 | 2/10 |
| 100 | 250 | 2/10 |
| 150 | 375 | 1/10 |
| 200 | 500 | 2/10 |

Acetaminophen, mg/kg + Glucosamine sulfate, mg/kg

| Acetaminophen | Glucosamine | No. protected/no. tested |
|---|---|---|
| 62.5 | — | 1/10 |
| 125 | — | 4/10 |
| 250 | — | 8/10 |
| 28.12 | 28.12 | 1/10 |
| 56.25 | 56.25 | 2/10 |
| 62.5 | 62.5 | 1/10 |
| 93.75 | 93.75 | 0/10 |
| 112.5 | 112.5 | 5/10 |
| 125 | 125 | 1/10 |
| 100 | 25 | 0/10 |
| 200 | 50 | 5/10 |
| 25 | 100 | 0/10 |
| 50 | 200 | 0/10 |
| 100 | 400 | 1/10 |

Diclofenac, mg/kg + Glucosamine sulfate, mg/kg[b]

| Diclofenac | Glucosamine | No. protected/no, tested |
|---|---|---|
| 1.144 | 125 | 5/20 |
| 2.288 | 250 | 6/10 |

Tramadol HCl, mg/kg + Glucosamine sulfate, mg/kg[c]

| Tramadol | Glucosamine | No. protected/no. tested |
|---|---|---|
| 6 | 150 | 1/10 |
| 10 | 250 | 3/10 |

TABLE 4-continued

Indomethacin, mg/kg + Glucosamine sulfate, mg/kg[d]

| Indomethacin | Glucosamine | No. protected/no. tested |
|---|---|---|
| 2.5 | — | 4/10 |
| 5.0 | — | 6/10 |
| 10.0 | — | 7/10 |
| 3.66 | 182.5 | 5/10 |

[a]ED50 (alone) = 109.2; ED50 (combination) = not determinable at the given dosages. Combination dosing does not reach the 50% response level.
[b]ED50 (alone) = 1.144; ED50 (combination) = 1.96
[c]ED50 (alone) = 8.05; ED50 (combination) not determinable at the given dosages. Combination dosing does not reach the 50% response level.
[d]ED50 (alone) = 3.66; ED50 (combination) = 3.66 (Additive)

What is claimed is:

1. An oral dosage form for treatment of the symptoms of pain comprising a glucosamine material and a therapeutic amount of an analgesic compound, wherein
    the weight ratio of glucosamine material to analgesic compound is such that the analgesic efficacy of the oral dosage form in alleviating the symptoms of pain when administered orally is greater than the analgesic efficacy of the analgesic compound alone at the dosage level for the analgesic compound,
    the glucosamine material is selected from the group consisting of α- or β-glucosamine or mixtures thereof, N-acetyl glucosamine, glucosamine sulfate, and glucosamine hydrochloride,
    the analgesic compound is ibuprofen or ketoprofen,
    and the weight ratio of glucosamine material to said analgesic compound is about 2:1 or more, said ratio being calculated based on glucosamine sulfate as the glucosamine material.

2. The dosage form of claim 1, wherein the weight ratio of glucosamine material to the analgesic compound is in the range of about 2:1 to 20:1.

3. The dosage form of claim 2 wherein the analgesic compound is ibuprofen.

4. The dosage form of claim 2 wherein the analgesic compound is ketoprofen.

5. The dosage form of claims 1 or 2 further comprising a therapeutic amount of an antiarthritic, antihistamine, muscle relaxant, sleep aid, decongestant, a bronchodilator, or a mixture thereof.

6. A method to alleviate the symptoms of pain in a human patient, which comprises orally administering to the patient a therapeutically effective amount of an oral dosage form of claims 1 or 2.

7. A method to alleviate the symptoms of pain comprising administering orally to a patient an oral dosage form, said oral dosage form consisting essentially of a therapeutic amount of an analgesic compound in admixture with a glucosamine material, wherein
    the analgesic compound is ibuprofen or ketoprofen,
    the glucosamine material is selected from the group consisting of α- or β-glucosamine, N-acetylglucosamine, glucosamine sulfate or glucosamine hydrochloride,
    the weight ratio of glucosamine material to analgesic compound is in the range of 2:1 up to 10:1, said ratio being calculated based on glucosamine sulfate as the glucosamine material and,
    at said ratio and dosage level, the analgesic efficacy of said dosage form is enhanced over the analgesic efficacy of the analgesic compound alone.

* * * * *